United States Patent [19]

Delseth et al.

[11] Patent Number: 4,581,297
[45] Date of Patent: Apr. 8, 1986

[54] USE OF METAL SALTS OF THIOSULPHURIC-S-ESTERS AS RUBBER/METAL BONDING PROMOTERS

[75] Inventors: Jean-Marc Delseth, Gembloux; Daniel E. Mauer, Chaumont-Gistoux; Philippe G. Moniotte, Heron, all of Belgium

[73] Assignee: Monsanto Europe, S.A., Brussels, Belgium

[21] Appl. No.: 692,481

[22] Filed: Jan. 18, 1985

[30] Foreign Application Priority Data

Jan. 20, 1984 [GB] United Kingdom ................ 8401508

[51] Int. Cl.$^4$ ............................................. B32B 15/06
[52] U.S. Cl. ..................................... 428/462; 260/400; 428/465; 428/492; 428/521; 524/83
[58] Field of Search ............... 428/492, 462, 465, 521; 524/83, 270; 260/400; 525/343

[56] References Cited

U.S. PATENT DOCUMENTS 2,921,083  1/1960  Gaertner ............................. 260/400
3,506,676  4/1970  Tesoro ................................. 524/83
3,535,249  10/1970 Larson ............................... 524/270
3,991,130  11/1976 Cowell ............................... 525/343
4,417,012  11/1983 Moniotte ............................. 524/83

Primary Examiner—Thomas J. Herbert
Attorney, Agent, or Firm—Gordon B. Seward

[57] ABSTRACT

The bond strength between a sulphur-vulcanizable rubber and a metal, especially brass, is increased by using as bonding promoter a compound having the formula $R-(CH_2)_a-S_2O_3^-M^+$ or a hydrate thereof, where a has an integral value of at least 1, and where (i) $M^+$ represents a sodium ion or an equivalent of a divalent nickel or cobalt ion and R represents hydroxy, cyano, chlorophenyl, fluorophenyl, nitrophenyl, alkoxyphenyl, alkylphenyl, dialkylphenyl, arylphenyl, naphthyl, alkylnaphthyl, benzoyl, phenoxy, halophenoxy, phthalimido, a group having the formula $R^2CONH-$, $R^2NHCO-$, where $R^2$ is an alkyl or aryl radical, $^+MOOC$, or 2,4-dihydroxy-6-pyrimidyl (or its keto-form equivalent) or (ii) $M^+$ is absent and R represents a grouping $^+H_3N-$.

16 Claims, No Drawings

USE OF METAL SALTS OF THIOSULPHURIC-S-ESTERS AS RUBBER/METAL BONDING PROMOTERS

This invention relates to rubber/metal composites and to certain novel compounds useful as rubber/metal bonding promoters.

Articles in which rubber is bonded to metal have been known for many years, and since the introduction of the steel-belted radial tire, rubber/metal bonding has been very extensively studied. It is known that certain substances will act as adhesion promoters to improve the initial adhesion level between the rubber and the metal and the maintenance of the adhesion level during accelerated laboratory ageing tests designed to simulate conditions to which the article may be subjected during its service life.

The main adhesion promoters currently used to promote the bonding of brass-coated steel to rubber are cobalt compounds, for example cobalt naphthenate, and resorcinol-and/or melamineformaldehyde resins used in conjunction with hydrated silica. Both of these types of adhesion promoters, which can be employed separately or in combination, have disadvantages, and alternative rubber/metal adhesion promoters to those currently employed are therefore desirable.

Our European Patent Application EP-A-0 109 955 discloses rubber/metal adhesion promoters of the general formula $$R^1-(S-SO_3M)_n$$

where $R^1$ represents an organic radical and M is a monovalent metal or the equivalent of a multivalent metal, and n has a value of from 1 to 4.

The present application relates to the use of compounds within the above general formula as rubber/metal bonding promoters, and to certain such compounds that are new. Specifically, the compounds useful according to the present invention are those having the formula $R-(CH_2)_a-S_2O_3-M+$ and their hydrates, where a has an integral value of at least 1, for example from 1 to 20, and where (i) M+ represents a sodium ion or an equivalent of a divalent nickel or cobalt ion and R represents hydroxy, cyano, chlorophyenyl, fluorophenyl, nitrophenyl, alkoxyphenol, alkylphenyl, dialkylphenyl, arylphenyl, naphthyl, alkylnaphthyl, benzoyl, phenoxy, halophenoxy, phthalimido, a group having the formula $R^2CONH-$, $R^2NHCO-$, where $R^2$ is an alkyl or aryl radical, + MOOC, or 2,4-dihydroxy-6-pyrimidyl (or its keto-form equivalent), or (ii) M+ is absent and R represents a grouping $+H_3N-$.

The invention includes a composite comprising a sulphur-vulcanisable rubber composition containing the rubber, sulphur, a vulcanisation accelerator, a component having a metal surface in contact with the composition, and, as a rubber/metal bonding promoter, a compound as defined above.

The invention further includes an article in which vulcanised rubber is bonded to a metal surface, the article having been obtained by heating a composite of the invention to vulcanisation temperature to vulcanise the rubber.

Most of the rubber/metal bonding promoters defined above are novel compounds, the exceptions being that M+ is not sodium when R represents cyano or +NaOOC and a is 2.

Within the above general formula, various sub-classes of compound are preferred, mainly because the starting materials required for their syntheses are more readily available than in some other instances. These sub-classes can be represented by the formulae $$HO(CH_2)_b-S_2O_3^-M^+,$$

where b=2-12;

$$NC(CH_2)_c-S_2O_3^-M^+,$$

where c=2-16;

$$R^3C_6H_4CH_2-S_2O_3^-M^+,$$

where $R^3$=Cl, F, NO_2, C_{1-12} alkyl, C_{1-12} alkoxy or phenyl;

$$(R^4)_2C_6H_3CH_2-S_2O_3^-M^+, \text{ where } R^4=C_{1-12} \text{ alkyl};$$

$$C_{10}H_7CH_2-S_2O_3^-M^+,$$

where $C_{10}H_7$ is naphthyl;

$$R^4C_{10}H_6CH_2-S_2O_3^-M^+, \text{ where } R^4C_{10}H_6 \text{ is } (C_{1-12}\text{alkyl})\text{naphthyl};$$

$$C_6H_5COCH_2-S_2O_3^-M^+,$$

$$R^5C_6H_4O(CH_2)_d-S_2O_3^-M^+,$$

where $R^5$=H or Halogen and d=1-12;

$$\text{Phthalimido}(CH_2)_e-S_2O_3^-M^+,$$

where e=1-12;

$$C_6H_5NHCO(CH_2)_f-S_2O_3^-M^+,$$

where f=1-12;

$$C_6H_5CONH(CH_2)_g-S_2O_3^-M^+,$$

where g=2-12;

$$+M^-OOC(CH_2)_h-S_2O_3^-M^+,$$

where h=1-12;

$$\text{"Uracyl" } CH_2-S_2O_3^-M^+,$$

where "Uracyl" represents 2,4-dihydroxy-6-pyrimidyl or its keto-form equivalent, and $$+H_3N(CH_2)_j-S_2O_3^-$$

where j=2-12.

In more preferred instances, b has a value of from 2 to 8; c has a value of from 2 to 8; d has a value of from 1 to 8; e has a value of from 1 to 8; f has a value of from 1 to 8; g has a value of from 2 to 8; h has a value of from 1 to 11; and j has a value of from 2 to 8.

Where, in the above formula, any of the symbols a to j has a value 2 or more, the alkylene group $(CH_2)_a$, $(CH_2)_b$ etc. can have a straight or branched chain. The substituents represented by $R^3$, $R^4$ and $R^5$ (when $R^5$ is halogen) can occupy any position in the nucleus in which they are substituents, but m- and p- substitution is generally preferred. When $R^3$ represents a $C_{1-12}$ alkyl or $C_{1-12}$ alkoxy group, this is preferably one containing from 1 to 8 carbon atoms. It can be straight- or branched chain group, for example methyl, ethyl, n-propyl, isopropyl, isobutyl, sec-butyl, t-amyl, isohexyl, or n-octyl, or a corresponding alkoxy group. Preferred and specific examples of the $C_{1-12}$ alkyl radical of a ($C_{1-12}$ alkyl)naphthyl group, of a group $R^4$ and of a group $R^2$ when this is an alkyl group, are the same as for $R^3$ above. $R^5$, when halogen, can be, for example, fluorine, chlorine or bromine.

As can be seen from the above formulae, the compounds are salts of thiosulphuric-S-esters, but they are named for convenience hereinbelow as organic thiosulphate salts. Specific examples of the compounds of the invention, in addition to those described in the examples below, are the sodium, cobalt and nickel salts of: 4-hydroxybutylthiosulphate, 5-hydroxypentylthiosulphate, 6-hydroxy-5-ethylhexylthiosulphate, 8-hydroxyoctylthiosulphate, 3-cyanopropylthiosulphate, 4-cyanobutylthiosulphate, 8-cyanooctylthiosulphate, o-chlorobenzylthiosulphate, m-chlorobenzylthiosulphate, m-fluorobenzylthiosulphate, m-nitrobenzylthiosulphate, p-methoxybenzylthiosulphate, m-ethoxybenzylthiosulphate, p-isopropoxybenzylthiosulphate, p-isoamyloxybenzylthiosulphate, m-2-ethylhexyloxybenzylthiosulphate, m-methylbenzylthiosulphate, p-ethylbenzylthiosulphate, p-n-propylbenzylthiosulphate, p-tert-butylbenzylthiosulphate, m-n-hexylbenzylthiosulphate, p-(1,1,3,3-tetramethylbutyl)benzylthiosulphate, m-phenylbenzylthiosulphate, p-(p-tolyl)benzylthiosulphate, 3,5-dimethylbenzylthiosulphate, 2-methyl-5-ethylbenzylthiosulphate, 2,5-diethylbenzylthiosulphate, 3,5-di-t-butylbenzylthiosulphate, (4-methyl-1-naphthyl)methylthiosulphate, (6-methyl-1-naphthyl) methylthiosulphate, (2-ethyl-1-naphthyl)methylthiosulphate, 3-phenoxypropylthiosulphate, 4-phenoxybutylthiosulphate, 5-phenoxypentylthiosulphate, 7-phenoxyheptylthiosulphate, o-chlorophenoxymethylthiosulphate, 2(o-chlorophenoxy)ethylthiosulphate, 2(p-chlorophenoxy)ethylthiosulphate, 3(p-bromophenoxy) propylthiosulphate, 4(p-bromophenoxy)butylthiosulphate, 6(m-chlorophenoxy)hexylthiosulphate, 5(p-fluorophenoxy)-3-methylpentylthiosulphate, phthalimidomethylthiosulphate, 2-phthalimidoethylthiosulphate, 4-phthalimidobutylthiosulphate, 8-phthalimidooctylthiosulphate, N-phenylcarboxamidomethylthiosulphate, 2(N-phenylcarboxamido)ethylthiosulphate, 3(N-phenylcarboxamido) propylthiosulphate, 4(N-phenylcarboxamido)butylthiosulphate, 6(N-phenylcarboxamido)hexylthiosulphate, 8(N-phenylcarboxamido) octylthiosulphate, 2(benzoylamino)ethylthiosulphate, 3(benzoylamino)propylthiosulphate, 4(benzoylamino)butylthiosulphate, 5(benzoylamino)pentylthiosulphate, 5(benzoylamino)-3-ethyl-pentylthiosulphate, 6(benzoylamino)-3,4-dimethylhexylthiosulphate, carboxymethylthiosulphate, 2-carboxyethylthiosulphate, 2-carboxypropylthiosulphate, 3-carboxypropylthiosulphate, 4-carboxybutylthiosulphate, 6-carboxyhexylthiosulphate, 5-carboxyheptylthiosulphate, 9-carboxynonylthiosulphate, 11-carboxyundecylthiosulphate, and the compounds of the formula $^+H_3N(CH_2)_j—S_2O_3—$ where the group $(CH_2)_j$ is ethylene, propylene, isopropylene, butylene, pentylene, 3-methylpentylene, heptylene or octylene.

The novel compounds of the invention that are sodium salts can be prepared by the nucleophilic substitution of halogen, usually chlorine or bromine, in an appropriate starting material having replaceable halogen atom, by reaction with sodium thiosulphate. The reaction is usually performed in water or in an aqueous alcoholic medium under reflux, but it may be advantageous to use reaction temperatures above the reflux temperatures of aqueous ethanol or methanol mixtures at normal pressures, by carrying out the reaction in an autoclave. For solubility reasons, aqueous ethanol or aqueous methanol is generally a more suitable reaction medium than the alcohol alone. Reaction times vary with the reaction temperature and the ease of replacement of the halogen atom. Typical reaction times for the replacement of chlorine at temperatures within the range 100°–150° C. are from 60 to 15 minutes. The solvent is then evaporated giving a residue which is essentially a mixture of the sodium salt of the organic thiosulphate and a sodium halide. Separation of these two components of the mixture can be effected by selective extraction with a solvent such as absolute ethanol in which the organic salt is significantly more soluble than the sodium halide.

Further details and possible variations in reaction conditions for the reaction between sodium thiosulphate and organic halides are described in our EP-A-0 070 143.

The compounds of the invention that are nickel salts are most conveniently prepared using the sodium salts as intermediates. For example displacement of the sodium ion can be effected by the introduction of a solution of the sodium salt of the organic thiosulphate into a column of cation-exchange resin in which the exchangeable ions are nickel. This procedure produces as a percolate a solution of the nickel salt of the organic thiosulphate from which the nickel salt in solid from, often containing water of crystallisation, can be obtained by evaporation of the percolate.

An alternative procedure comprises mixing the sodium organic thiosulphate and a nickel salt in a solvent in which both are at least moderately soluble but in which the by-product sodium salt has low solubility. Absolute methanol can be used as such a solvent in some instances.

The bonding promoters of the invention are especially effective in compositions in which the rubber is cis-polyisoprene, either natural or synthetic, and in blends containing at least 25% by weight of cis-polyisoprene with other rubbers. Preferably the rubber, if a blend, contains at least 40% and more preferably at least 60% by weight of cis-polyisoprene. Examples of other rubbers which may be blended with cis-polyisoprene include poly-1,3-butadiene, copolymers of 1,3-butadiene with other monomers, for example styrene, acrylonitrile, isobutylene and methyl methacrylate, ethylene-propylene-diene terpolymers, and halogen-containing rubbers such as chlorobutyl, bromobutyl and chloroprene rubbers.

In the compositions of the invention the esssential vulcanising agent is sulphur, but other vulcanising agents such as amine disulphides need not be excluded. The amount of sulphur in the compositions is typically from 2 to 6 parts, for example from 3 to 6, by weight per 100 parts by weight of rubber, but lesser or larger amounts, for example from 1 to 7 or 8 parts on the same basis, may be employed. A preferred range is from 2.5 to 4 parts per 100 parts by weight of rubber. An advantage of the bonding promoters of the invention over the conventionally-used cobalt compounds is that they are effective at lower sulphur levels. The principal significance of this is that over the range of sulphur levels that gives vulcanisates of acceptable physical properties, those vulcanisates prepared using lower levels of sulphur show greater resistance to reversion and oxidative ageing than those prepared using higher levels of sulphur.

Examples of vulcanisation accelerators which can be used in the present invention are the thiazole-based accelerators, for example 2-mercaptobenzothiazole,-bis(2-benzothiazolyl)disulphide, 2(2',4'-dinitrophenylthio)benzothiazole, benzothiazole-2-sulphenamides for instance N-isopropyl-benzothiazole-2-sulphenamide, N-tert-butyl-benzothiazole-2-sulphenamide, N-cyclohexylbenzothiazole-2-sulphenamide, and 2(morpholinothio) benzothiazole, and thiocarbamylsulphenamides, for example N,N-dimethyl-N',N'-dicyclohexyl-thiocarbamyl-sulphenamide and N(morpholinothiocarbonylthio) morpholine. A single accelerator or a mixture of accelerators may be used. Best results are usually obtained using the benzothiazole-2-sulphenamides, especially those with relatively long induction times, for example N,N-dicyclohexyl-benzothiazole -2-sulphenamide and 2(morpholinothio)benzothiazole. In the compositions of the invention, these are usually used in amounts of from 0.3 to 2, for example from 0.3 to 1.5, preferably from 0.4 to 1.0 and more preferably from 0.5 to 0.8, parts by weight per 100 parts by weight of rubber.

The bonding promoters defined above are very effective in promoting bonding between rubber and brass, for example the bonding between rubber and brass-coated steel. The brass typically has a copper content of from 60 to 70% by weight, more especially from 63 to 68% by weight, with the optimum percentage depending on the particular conditions under which the bond is formed. The brass coating on brass-coated steel can have a thickness of, for example, from 0.05 to 1 micrometer, preferably from 0.07 to 0.7 micrometer, for example from 0.15 to 0.4 micrometer. Rubber can also be bonded effectively to alloys of copper and zinc containing small amounts of one or more other metals, for example cobalt, nickel or iron.

Mixtures of different compounds of the above formula can be used as bonding promoters in a composite of the invention. Moreover, it is possible to use a mixture of such a compound with one or more of the organic thiosulphates (which may contain more than one thiosulphate group) disclosed in EP-A-0 109 955. In a further variation, a compound of the invention, for example a sodium salt, can be used as a co-promoter with a cobalt-containing rubber/metal bonding promoter other than a cobalt organo-thiosulphate e.g. cobalt naphthenate.

The amount of bonding promoter which, as indicated above, may be a single compound or a mixture, employed in the present invention is usually from 0.1 to 6 parts by weight, and preferably from 0.5 to 4, for example from 2 to 4, parts by weight of rubber.

The bonding promoters used in this invention can be incorporated into rubber by conventional mixing procedures, for example by adding them in a Banbury mixer or by adding them to the rubber on a mill. Ordinarily, with liquid or low melting solid additives, no special precautions are necessary for obtaining good dispersions. However, when using higher melting solids it is recommended that they be ground to a fine powder, preferably 70 micrometer particle size or less, to ensure adequate dispersion. In certain instances, it is convenient to add a solid promoter as a predispersion of particulate material in a rubber-compatible hydrocarbon oil or polymer, for example EPDM rubber.

Additives which are conventionally present in rubber compositions which are to be bonded to metal, are normally used in the vulcanisable compositions of the present invention. Such additives include carbon black, usually a carbon black of the N300 series such as N347 or N326, which typically is used in an amount of from 40 to 70 parts by weight per 100 parts by weight of rubber. Other such additives are, for example, zinc oxide, which may be used in an amount of, for instance, from 2 to 10 or from 4 to 10 parts by weight per 100 parts by weight of rubber; stearic acid at a level of, for instance, from 0.5 to 2, for example from 1 to 2, parts by weight per 100 parts by weight of rubber; hydrocarbon softeners and extender oils; antidegradants, for example N-alkyl-N'-phenyl-p-phenylenediamines; and tackifiers. Other fillers may be used, for example silica, and the rubber stocks may also contain metal oxide activators other than zinc oxide, for example magnesium oxide, other bonding agents or promoters, for example phenolic, resorcinol and/or melamine adhesive resins, prevulcanisation inhibitors, for instance N-cyclohexylthiophthalimide, and corrosion inhibitors, for example inhibitors based on boric acid, organic borates, inorganic borates such as sodium tetraborate, inorganic phosphates and chromates. The metal surface to which the rubber is to be bonded can be subjected to various pre-treatments, for example to ensure complete cleanliness or to confer corrosion resistance.

Evaluation of the adhesion promoters was carried out using a vulcanisable rubber composition of a type known as "skimstock" as follows:

|  | Parts by weight |
| --- | --- |
| Natural rubber | 100 |
| N 347 carbon black | 55 |
| Zinc Oxide | 8 |
| Stearic Acid | 2 |
| Process Oil | 3 |
| Tackifier | 3 |
| Antiozonant[(1)] | 2 |
| Antioxidant[(2)] | 1 |
| Sulphur | 4 |
| Accelerator[(3)] | 0.7 |
| Bonding promoter | 1 |

[(1)]N—1,3-dimethylbutyl-N'—phenyl-p-phenylenediamine
[(2)]Polymerised 2,2,4-trimethyl-1,2-dihydroquinoline
[(3)]2(morpholinothio)benzothiazole.

Mixing of the components except sulphur and accelerator was done in a laboratory scale Banbury mixer having a capacity of 1.57 liter and operating at a filling factor of about 0.8 and a rotor speed of 117 r.p.m., according to the following schedule:

| Time (mins.) | |
| --- | --- |
| 0 | Rubber placed in mixer and rotors started. |
| 1 | Half carbon black and zinc oxide added. |
| 2.5 | Remainder of carbon black, stearic acid, process oil, tackifier, antiozonant, antioxidant, bonding promoter added. |
| 4 | Sweep |
| 5 | Dumped at temperature 150 ± 5° C. |

The batch was then transferred to a mill at 70°–75° C. for sheeting off. Sulphur and accelerator were added to portions of the masterbatch on a mill as required.

The metal component was a typical brass-coated steel tire cord having the construction 3+9+15×0.175+1, each cord having a coating of brass, approximately 0.20 micrometer thick, with an average copper content of 63.5% by weight.

Rubber/metal bond strengths were measured using the adhesion test described by R. C. Ayerst and E. R. Rodger, Rubber Chem. Technol. 45, 1497(1972). In this method, adhesion blocks are prepared in a similar manner to that specified in ASTM D-2229, but using clamping plates to hold the cords in the mould to maintain alignment during cure, and a frame for pre-loading and uniformly stressing the cord before mould building. The adhesion block comprises a strip of rubber having one end each of several uniformly-spaced lengths of cord embedded in one edge of the strip, and a similar array of lengths of cord, each length having one end embedded in the edge of the strip opposite the first edge and in staggered relationship to the cords in the first edge. Pullout adhesion is measured on a tensile tester by arranging the adhesion block so that the cords are vertical and the rubber strip horizontal, and by holding two lower wires and pulling out the upper wire between them at a crosshead speed of 5 cm/min. The pullout force recorded is the mean of the values for each of the several upper cords except those at each end of the strip, which are not taken into account in order to eliminate possible end effects. Where the pullout force exceeds the breaking load of one or more of the wires in the test procedure, this is signified in the Tables by the symbol >.

The results given in the tables below under the headings "Initial Adhesion", "Steam Ageing" and "Salt Bath Ageing" were obtained in adhesion blocks where the rubber was cured at 145° C. for $T_{90}+5$ minutes, "$T_{90}$" being the time in minutes taken for a sample of the same rubber cured in a rheometer (British Standard Test Method 1673 Part 10) to reach 90% of the maximum modulus. Blocks that were "steam aged" were kept in steam under pressure at 120° C. for 8 hours and those that were "salt bath aged" were immersed in a 5% sodium chloride solution at 90° C. for 48 hours after curing and before testing.

In "Steel Cord: Analysis of Used Truck Tires and Simulation of the Found Phenomena in Laboratory Experiments" an article in "Tire Reinforcement and Tire Performance", ASTM STP 694, R. A. Fleming and D. I. Livingston, Eds, American Society for Testing and Materials, 1979, pp 69-86, C. C. J. de Jong concludes that in evaluating tires and other composites containing metal and cord reinforcement, attention should be paid to aged adhesion rather than to initial adhesion. The ageing conditions mentioned above are similar to those proposed by de Jong to simulate, at an enhanced level, various conditions which might be encountered during the service life of a tire.

The compounds of the invention and their preparation are illustrated by the following Examples

EXAMPLE 1

Sodium 2-hydroxyethylthiosulphate

2-Bromoethanol (52.9 g) was added to sodium thiosulphate pentahydrate (106.7 g) in ethanol (150 ml) and water (150 ml) and the mixture was refluxed for 30 minutes. The solution was evaporated to dryness under reduced pressure, giving a solid residue. This was heated under reflux with absolute methanol (400 ml) and the mixture was filtered hot. The filtrate was cooled to −20° C. giving a first crop of crystals which were separated by filtration. The filtrate was concentrated and then recooled to −20° C. giving a second crop of crystals. The combined weight of the first and second crops was 59 g.

| NMR analysis of a sample showed | |
|---|---|
| Organic thiosulphate | 98.3% |
| Water | 1.7% |

EXAMPLE 2

Sodium 6-hydroxyhexylthiosulphate

A stirred mixture of sodium thiosulphate pentahydrate (79.4 g, 0.32 mole) and 93% pure 6-bromophexanol (58 g, 0.30 mole) in water (100 ml) and ethanol (100 ml) was heated under relux. After 10 minutes at the boiling point a homogenous solution was obtained. Refluxing was continued for a further 5 minutes and the solution was then cooled to room temperature. The solvent was evaporated under vacuum until crystallisation began, and the solution was then cooled further to 4° C. Filtration gave 52.6 g of a white solid. The solid (43 g) was purified by heating to about 50° C. with absolute ethanol (400 ml), and filtering the solution at this temperature to remove undissolved solid. The filtrate was left at room temperature until crystallisation began and was then kept at refrigerator temperature for a further 12 hours. Filtration afforded 28 g of product.

| NMR analysis showed | |
|---|---|
| Organic thiosulphate | 99.1% |
| Water | 0.9% |
| Total accounted for 92%. | |

EXAMPLE 3

Nickel 6-hydroxyhexylthiosulphate

A cation-exchange resin, Amberlite ® IRN 77, (230 ml) was charged to a column and washed by passing distilled water through the column. A solution of nickel chloride hexahydrate (100 g per liter of water) was then supplied to the top of the column and the supply was continued until the percolate leaving the base of the column appeared coloured. The column was then washed with water. The water wash was followed by a solution of sodium 6-hydroxyhexylthiosulphate (12 g) in water (200 ml). After collecting the percolate from the base of the column, the solution was evaporated under reduced pressure and finally desiccated under vacuum giving a solid residue (9.3 g).

NMR analysis showed organic thiosulphate, 90.7%; water 9.1%; total accounted for 97%.

The percentage Ni was determined by titration with ethylene diamine tetracetic acid (EDTA) solution. A result of 5.50% was obtained compared with a calculated value of 10.01% for nickel 6-hydroxyhexylthiosulphate hexahydrate, showing that the ion-exchange was incomplete.

EXAMPLE 4

Sodium 2-cyanoethylthiosulphate

A stirred mixture of 3-bromopropionitrile (71.6 g), sodium thiosulphate pentahydrate (137.9 g), ethanol (50 ml) and water (50 ml) was boiled under reflux for 1.5 hours. The solution was then allowed to cool, and the solvents were evaporated under vacuum, giving a white solid residue. Further unbound water was removed by adding ethanol to the residue and again evaporating the solvent under vacuum. The residue was stirred with hot ethanol (800 ml), and the suspension thus obtained was filtered while hot. On cooling, the filtrate deposited a white solid (80 g).

NMR analysis of the solid showed that it contained 95.4% by weight of sodium 2-cyanoethylthiosulphate and 4.6% by weight of water.

EXAMPLE 5

Nickel 2-cyanoethylthiosulphate

Anhydrous nickel chloride (0.1 mole) and absolute methanol (100 ml) were refluxed with stirring for 20 minutes, giving a clear solution, which was then cooled to 40° C. Sodium 2-cyanoethylthiosulphate, prepared as described above and dried under vacuum (0.2 mole) was then added to the solution with stirring, and stirring at 40° C. was continued for 1 hour. During this time sodium chloride was precipitated. The suspension was filtered and the filtrate was evaporated giving nickel 2-cyanoethylthiosulphate as a residue.

EXAMPLE 6

Sodium p-fluorobenzylthiosulphate p-Fluorobenzyl bromide (25 g) and sodium thiosulphate pentahydrate (35 g) were added to ethanol (100 ml) and water (100 ml). The mixture was refluxed for 1 hour, at which time it was homogeneous. The solution was allowed to cool to 50° C., and solvent was then evaporated at 40°–50° C. under reduced pressure. A solid started to crystallise, the resulting suspension was cooled to 4° C. and was allowed to stand at this temperature undisturbed. Filtration, and drying of the solid gave 23.5 g of crystals having an IR spectrum showing the three characteristic absorptions of organic thiosulphate-S-esters at circa 1200 cm$^{-1}$ (very strong), 1050–1020 (strong) and 620–650 (strong).

EXAMPLE 7

Nickel p-fluorobenzylthiosulphate

Sodium p-fluorobenzylthiosulphate (12 g) was dissolved in distilled water (200 ml). The solution was filtered to remove slight turbidity, and the filtrate was poured into the top of a column of nickel-containing cation-exchange resin prepared as described in Example 3. The solution collected from the base of the column was evaporated under reduced pressure at 30°–35° C. until most of the water was removed, and the residue was dried under vacuum at room temperaature giving 12.8 g of solid. Its nickel content, determined by titration with EDTA, was 10.09%, compared with a calculated value of 9.67% for nickel p-fluorobenzylthiosulphate hexahydrate.

EXAMPLE 8

Sodium p-nitrobenzyl thiosulphate

This compound was prepared from p-nitrobenzyl bromide (30 g) and sodium thiosulphate pentahydrate (36.2 g) by a procedure similar to that described in Example 6. White crystals (33.6 g) were obtained. The IR showed the three characteristic absorptions of organic thiosulphate-S-esters identified in Example 6.

EXAMPLE 9

Nickel p-nitrobenzylthiosulphate

A solution of sodium p-nitrobenzylthiosulphate (12 g) in water (350 ml) was fed dropwise to the top of a column of a nickel-containing cation-exchange resin prepared as described in Example 3, and percolate was collected at the base of the column. When percolation was complete, most of the water was evaporated and the residue was dried under vacuum, giving 12.1 g of nickel salt.

The IR spectrum showed the three characteristic absorptions of organic thiosulphate-S-esters. NMR analysis gave organic thiosulphate 86.7%; water 13.3%; total accounted for 97%.

EXAMPLE 10

Sodium m-methoxybenzylthiosulphate m-Methoxybenzyl chloride (23 g) was added to sodium thiosulphate pentahydrate (41.6 g) in ethanol (50 ml) and water (50 ml), and the mixture was heated under reflux for 1 hour. The solution was cooled to $-20°$ C. and crystallisation occurred after induction by shaking. The crystals were collected by filtration and then dried under vacuum giving a yield of 36.6 g.

The IR spectrum showed the three characteristic absorptions of organic thiosulphate-S-esters, and NMR analysis gave organic thiosulphate 93.6%; water 6.4%; total accounted for 96%.

EXAMPLE 11

Nickel m-methoxybenzylthiosulphate

This compound was obtained from sodium m-methoxybenzylthiosulphate (12 g dissolved in water, 500 ml) by a procedure similar to that described in Example 3. 13.0 g of the nickel salt were obtained.

The content of nickel found by titration with EDTA was 10.67% compared with a calculated content 9.77% for nickel m-methoxybenzylthiosulphate hexahydrate.

EXAMPLE 12

Sodium p-methylbenzylthiosulphate

Alpha-bromo-p-xylene (23 g) was added to sodium thiosulphate pentahydrate (35.5 g) in ethanol (50 ml) and water (50 ml), and the mixture was heated under reflux for 90 minutes. The solution was cooled to 3° C. when crystals appeared. After some hours at this temperature, the crystals were collected by filtration and dried under vacuum giving a yield of 32.9 g.

The IR spectrum showed the three characteristic absorptions of organic thiosulphate-S-esters and NMR analysis gave organic thiosulphate 97.5%; water 2.5%.

EXAMPLE 13

Sodium 2,5-dimethylbenzylthiosulphate

This compound was prepared from 2,5-dimethylbenzyl chloride (25 g) and sodium thiosulphate pentahydrate (42.3 g) by a procedure similar to that described in Example 12. The yield was 40.4 g.

Its IR spectrum had absorptions characteristic of organic thiosulphate-S-esters and NMR analysis showed organic thiosulphate 92.1%; water 7.9%.

EXAMPLE 14

Sodium benzoylmethylthiosulphate

This compound was prepared by a procedure similar to that of Example 6, from alpha-bromoacetophenone (40 g) and sodium thiosulphate pentahydrate (55 g). Cream-coloured crystals were collected (38 g).

IR spectrum showed the characteristic features for organic thiosulphate-S-esters, and a C=O absorption band at 1670 cm$^{-1}$.

EXAMPLE 15

Sodium 2-phenoxyethylthiosulphate

This compound was prepared from 2-phenoxyethyl bromide (40.2 g) and sodium thiosulphate pentahydrate (50 g) in ethanol (200 ml) and water (200 ml) by a procedure similar to that described in Example 6. The yield of product, in the form of white crystals, was 45 g.

The IR spectrum of the product had absorptions characteristic of organic thiosulphate-S-esters.

EXAMPLE 16

Sodium 2(p-bromophenoxy)ethylthiosulphate

This compound was obtained from 2(p-bromophenoxy)ethyl bromide (25 g) and sodium thiosulphate pentahydrate (23 g) by a procedure essentially the same as that described in Example 6. The yield of product was 31 g in the form of white crystals.

EXAMPLE 17

Nickel 2(p-bromophenoxy)ethylthiosulphate

This compound was obtained from a solution of sodium 2(p-bromophenoxy)ethylthiosulphate (10.35 g) dissolved in water (600 ml) by a procedure similar to that described in Example 3. The percolate collected at the base of the column was evaporated and the residue was dried under vacuum, giving 7.7 g of solid.

Determination of the nickel content of the solid by titration with EDTA gave a figure of 6.09% compared with a figure calculated for the hexahydrate of 7.42%.

EXAMPLE 18

Sodium 3-phthalimidopropylthiosulphate

N(3-Bromopropyl)phthalimide (30 g) was added to sodium thiosulphate pentahydrate (29.2 g) in water (100 ml) and ethanol (100 ml), and the mixture was heated under reflux for 30 minutes. The solvents were then evaporated until crystals appeared, after which the solution was cooled to 3° C. and kept at that temperature for 18 hours. The crystals which had formed were collected by filtration. Cooling the filtrate to −20° C. gave, after shaking to induce crystallisation, a further crop of crystals. After 18 hours at −20° C., the crystals were separated by filtration, giving a combined yield of first crop and second crop crystals of 26.4 g.

The IR spectrum of the product showed absorptions characteristic of organic thiosulphate-S-esters. NMR analysis gave Organic thiosulphate 92.9%; water 7.1%; total accounted for 91%.

EXAMPLE 19

Sodium 5(N-phenylcarboxamido)pentylthiosulphate

A mixture of N-phenyl-6-bromohexanoamide (54 g, 0.2 mole), sodium thiosulphate (55 g, 0.22 mole) in water (250 ml) and ethanol (250 ml) was boiled under reflux for 2 hours. The resulting homogeneous solution was partially evaporated under reduced pressure, and the remaining solution was cooled to 3° C. and kept at that temperature for 18 hours. White crystals formed which were collected by filtration. Yield 60 g.

EXAMPLE 20

Sodium 6(Benzoylamino)hexylthiosulphate

6-Bromohexylamine hydrobromide (26.1 g, 0.1 mole) was gradually added to 2N NaOH solution (150 ml) kept at 10° C. by external cooling. While maintaining this temperature, benzoyl chloride (16.8 g, 0.12 mole) was added in portions with efficient stirring. Stirring was continued after the addition was complete, the temperature being allowed to rise to 20° C. AfTer 30 minutes, the white crystalline precipitate, i.e. 6(benzoylamino) hexylbromide which had formed during the process, was separated by filtration and washed with water.

The 6(benzoylamino)hexyl bromide thus obtained was added to water (100 ml), ethanol (100 ml) and sodium thiosulphate pentahydrate (37.2 g, 0.15 mole), and the mixture was boiled under reflux for 25 minutes. The solution thus obtained was evaporated to dryness under reduced pressure. The residue was extracted with ethanol (500 ml) by boiling under reflux for 10 minutes, the extract was filtered and the filtrate was concentrated to a volume of about 80 ml and then cooled to −20° C. Crystals formed, and after 18 hours at −20° C., they were separated by filtration andwere washed on the filter with a mixture of ethanol and ether. Yield 22 g.

EXAMPLE 21

5-Carboxypentanethiosulphate, disodium salt

A solution of 6bromohexanoic acid (100 g) in ethanol (150 ml) and water (150 ml) was neutralised by the addition of 2N NaOH. This solution was added to sodium thiosulphate pentahydrate (133.6 g), and the mixture was boiled under reflux for 3 hours. The solvents were then evaporated under reduced pressure until crystals appeared, and the solution was then cooled to 3° C. After 18 hours, the crystals were collected by filtration and dried under vacuum.

The IR spectrum showed absorptions characteristic of organic thiosulphate-S-esters. NMR analysis gave organic thiosulphate 92.5%; water 7.5%; total accounted for 75%.

EXAMPLE 22

10-Carboxydecanethiosulphate, disodium salt

11- Bromoundecanoic acid (49 g) suspended in a stirred mixture of ethanol (200 ml) and water (200 ml) was neutralised by the addition of 2N NaOH solution. Sodium thiosulphate pentahydrate(50 g) was added, and the mixture was refluxed for 2 hours.

It was then evaporated to dryness, and the residue was extracted twice with ethanol (400 ml) under reflux. Each extract gave a pale yellow precipitate on cooling to −20° C. The precipitate (total 55 g) was collected by filtration. Analysis of the precipitate by NMR showed:
10-carboxydecanethiophenyl, disodium salt 80%
Water 9.2%
Sodium bromide (by difference) 11%

EXAMPLE 23

10-Carboxydecanethiosulphate, nickel salt

The disodium salt of Example 22 (10 g) in water (50 ml) was treated with a slight excess of barium chloride thus precipitating the barium salt of 10-carboxydecanethiosulphate. This was separated by filtration and then resuspended in water. A stoichiometric amount of nickel sulphate hexahydrate was added, and the mixture was allowed to stir for about 8 hours. Filtration and evaporation of the filtrate gave a green, waxy solid.

EXAMPLE 24

$^+NH_3$—$(CH_2)_6$—$S_2O_3^-$ Internal salt of 6-aminohexylthiosulphuric S-ester 6-Bromohexylamine hydrobromide (25 g) was added to a solution of sodium thiosulphate (24.4 g) in water (580 ml), and the mixture was heated under reflux for 30 minutes. The solution was then evaporated to half its volume and allowed to cool. A precipitate formed and was collected by filtration. The solid on the filter was washed with water (150 ml), acetone (50 ml) and ether (130 ml), and then dried under vacuum. Yield 12.6 g. The IR spectrum was consistent with the expected structure.

EXAMPLE 25

Sodium (2,4-dihydroxypyrimid-6-yl)methylthiosulphate

A mixture of 6-(chloromethyl)uracil (32 g, 0.2 mole) and sodium thiosulphate pentahydrate (51.6 g, 0.208 mole) in water (100 ml) and ethanol (100 ml) was heated under reflux. After 10 minutes, the mixture became homogeneous, and the solution was then boiled for a further 5 minutes. After cooling somewhat, the solvents were evaporated under reduced pressure. Water (30 ml) was added to the solid residue, and after standing overnight at 0° C., white crystals (54.9 g) were isolated by filtration. NMR spectrum showed organic thiosulphate 81.9%; water 18.1%.

EXAMPLE 26

Sodium p-phenylbenzylthiosulphate 4-chloromethylbiphenyl (20 g; 0.1 mole) and sodium thiosulphate pentahydrate (27 g; 0.11 mole) in water (60 ml) and ethanol ((60 ml) were refluxed for ½ hour. The cooled reaction mixture was filtered, and the solid was washed with water and dried to yield white product (14.2 g) containing 86% of the organic thiosulphate.

EXAMPLE 27

Nickel p-phenylbenzylthiosulphate

A solution of the product of Example 26 (13 g) in absolute methanol (800 ml) was added to a solution of nickel dichloride hexahydrate (5.2 g) in absolute methanol (100 ml). The green solution was evaporated to dryness. The residue was washed with water to remove sodium chloride, giving the hydrated green product (13.5 g).

EXAMPLE 28

Cobalt p-phenylbenzylthiosulphate

This product was obtained by the method described for the nickel analogue of Example 27, but with cobalt dichloride hexahydrate (5.2 g) replacing the nickel chloride hexahydrate. There was obtained a purple product (12.5 g).

EXAMPLE 29

Sodium p-chlorobenzylthiosulphate p-Chlorobenzyl chloride (72.5 g; 0.45 mole) and sodium pentahydrate (124 g; 0.5 mole) in water (150 ml) and ethanol (150 ml) were refluxed for 1 hour. The reaction mixture was allowed to cool and the precipitate was separated by filtration. Recrystallisation from methanol yielded 71 g of product essentially 100% pure by H'NMR.

EXAMPLE 30

Nickel p-chlorobenzylthiosulphate

The product from Example 29 (26 g) in absolute methanol (500 ml) was treated with nickel dichloride hexahydrate (11.8 g.) dissolved in absolute methanol (150 ml). The green solution was evaporated until sodium chloride separated, and the mixture was then filtered. Evaporation of the filtrate to dryness gave a green solid (34.5 g) containing 12% Ni.

EXAMPLE 31

Sodium (1-naphthyl)methylthiosulphate

1-Chloromethylnaphthalene (0.6 mole) and sodium thiosulphate pentahydrate (0.6 mole) in water (200 ml) and ethanol (200 ml) were refluxed for 45 minutes. The cooled reaction mixture was filtered, and the solid collected was the crude product (140 g). This was extracted with hot methanol. Evaporation of the methanolic extracts and drying of the solid residue gave the organic thiosulphate.

EXAMPLE 32

Nickel (1-naphthyl)methylthiosulphate

The product from Example 31 in absolute methanol (500 ml) was treated with nickel dichloride hexayhydrate (11.8 g) in absolute methanol (200 ml.) The green solution was evaporated to small bulk and the sodium chloride was separated by filtration. Evaporation to dryness yielded a green product (31 g).

EXAMPLE 33

Cobalt (1-naphthyl)methylthiosulphate

This compound was prepared by the procedure of Example 32, but with the nickel dichloride hexahydrate replaced by cobalt dichloride hexahydrate (11.8 g).

EXAMPLE 34

Sodium(2-methyl-1-naphthyl)methylthiosulphate 1-chloromethyl-2-methylnaphthalene (25 g; 0.13 mole) and sodium thiosulphate pentahydrate (35.8 g; 0.14 mole) in water (75 ml) and ethanol (75 ml) were refluxed for 1½ hours. The white precipitate was collected by filtration, washed with water and dried to yield the hydrated organic thiosulphate (34 g) of essentially 100% purity.

The following table gives results obtained in the evaluation of various rubber/metal bonding promoters as set out below.

| Promoter number in Table | Name or formula (excluding possible water of crystallisation) |
|---|---|
| 1 | $HO(CH_2)_2S_2O_3Na$ |
| 2 | $HO(CH_2)_6S_2O_3Na$ |
| 3 | $[HO(CH_2)_6S_2O_3]_2Ni$ |
| 4 | $NC(CH_2)_2S_2O_3Na$ |
| 5 | $[NC(CH_2)_2S_2O_3]Ni$ |
| 6 | p-Fluorobenzylthiosulphate, sodium salt |
| 7 | p-Fluorobenzylthiosulphate, nickel salt |
| 8 | p-Nitrobenzylthiosulphate, sodium salt |
| 9 | p-Nitrobenzylthiosulphate, nickel salt |
| 10 | m-Methoxybenzylthiosulphate, sodium salt |
| 11 | m-Methoxybenzylthiosulphate, nickel salt |
| 12 | p-Methylbenzylthiosulphate, sodium salt |
| 13 | 2,5-dimethylbenzylthiosulphate, sodium salt |
| 14 | Benzoylmethylthiosulphate, sodium salt |
| 15 | 2-Phenoxyethylthiosulphate, sodium salt |
| 16 | p-Bromophenoxyethylthiosulphate, sodium salt |
| 17 | p-Bromophenoxyethylthiosulphate, nickel salt |
| 18 | 3-Phthalimidopropylthiosulphate, sodium salt |
| 19 | $C_6H_5NHCO(CH_2)_5S_2O_3Na$ |
| 20 | $C_6H_5CONH(CH_2)_6S_2O_3Na$ |
| 21 | $NaO_2C(CH_2)_5S_2O_3Na$ |
| 22 | $NaO_2C(CH_2)_{10}S_2O_3Na$ |
| 23 | $[O_2C(CH_2)_{10}S_2O_3]Ni$ |
| 24 | $^+H_3N(CH_2)_6S_2O_3^-$ |
| 25 | 2,4-dihydroxy-6-pyrimidyl-CH$_2$S$_2$O$_3$Na (keto form) |

TABLE

| PROMOTER | Pull-out force in Newtons/cm | | |
|---|---|---|---|
| | INITIAL ADHESION | STEAM AGEING | SALT BATH AGEING (48 Hours) |
| None | >480 | >570 | 200 |
| 1 | >490 | >510 | 280 |
| 2 | >500 | >530 | 300 |
| 3 | >520 | >500 | 300 |
| 4 | >500 | 480 | 250 |
| 5 | >580 | 320 | 330 |
| 6 | >480 | 510 | 200 |
| 7 | >490 | >510 | 330 |
| 8 | >480 | 530 | 260 |
| 9 | >490 | >530 | 290 |
| 10 | >490 | >510 | 250 |
| 11 | >490 | >480 | 320 |
| 12 | >490 | 390 | 280 |
| 13 | >550 | >450 | 460 |
| 14 | >500 | 510 | 270 |
| 15 | >480 | >490 | 260 |
| 16 | >480 | >560 | 260 |
| 17 | >570 | >470 | 390 |
| 18 | >520 | >510 | 400 |
| 19 | >470 | >500 | 440 |
| 20 | >470 | >510 | 290 |
| 21 | >580 | 460 | 200 |
| 22 | >490 | 560 | 170 |
| 23 | >480 | 460 | 290 |
| 24 | >490 | >510 | 320 |
| 25 | >490 | >510 | 400 |

We claim:

1. A composite comprising a sulphur-vulcanisable rubber composition containing the rubber, sulphur, a vulcanisation accelerator and a rubber/metal bonding promoter, and a component having a metal surface in contact with the said composition, characterised in that the bonding promoter comprises a compound having the formula $R—(CH_2)_a—S_2O_3^-M^+$ or a hydrate thereof, where a has an integral value of at least 1, and where (i) $M^+$ represents a sodium ion or an equivalent of a divalent nickel or cobalt ion and R represents hydroxy, cyano, chlorophenyl, fluorophenyl, nitrophenyl, alkoxyphenyl, alkylphenyl, dialkylphenyl, arylphenyl, naphthyl, alkylnaphthyl, benzoyl, phenoxy, halophenoxy, phthalimido, a group having the formula $R^2CONH—$, $R^2NHCO—$, where $R^2$ is an alkyl or aryl radical, $^+MOOC$, or 2,4-dihydroxy-6-pyrimidyl (or its keto-form equivalent) or (ii) $M^+$ is absent and R represents a grouping $^+H_3N—$.

2. A composite according to claim 1 in which the bonding promoter comprises a compound having the formula $$HO(CH_2)_b—S_2O_3^-M^+ \text{ or } NC(CH_2)_c—S_2O_3^-M^+$$

or a hydrate thereof, where b=2–12 and c=2–16.

3. A composite according to claim 1 in which the bonding promoter comprises a compound having the formula $$R^3C_6H_4CH_2—S_2O_3^-M^+ \text{ or}$$
$$(R^4)_2C_6H_3CH_2—S_2O_3^-M^+$$

or a hydrate thereof, where $R^3$=Cl, F, NO$_2$, C$_{1-12}$ alkyl, C$_{1-12}$ alkoxy or phenyl and $R^4$=C$_{1-12}$ alkyl.

4. A composite according to claim 1 in which the promoter comprises a compound having the formula $$C_{10}H_7CH_2S_2O_3^-M^+ \text{ or } R^4C_{10}H_6CH_2S_2O_3^-M^+$$

or a hydrate thereof, where $C_{10}H_7$ is naphthyl and $R^4C_{10}H_6$ is (C$_{1-12}$ alkyl)naphthyl.

5. A composite according to claim 1 in which the promoter comprises a compound having the formula $$C_6H_5COCH_2—S_2O_3^-M^+ \text{ or}$$
$$R^5C_6H_4O(CH_2)_d—S_2O_3^-M^+$$

or a hydrate thereof where $R^5$=H or halogen and d=1–12.

6. A composite according to claim 1 in which the promoter comprises a compound having the formula $$C_6H_5NHCO(CH_2)_f—S_2O_3^-M^+ \text{ or}$$
$$C_6H_5CONH(CH_2)_g—S_2O_3^-M^+$$

or a hydrate thereof, where f=1–12 and g=2–12.

7. A composite according to claim 1 in which the promoter comprises a compound having the formula (Phthalimido)(CH$_2$)$_e$—S$_2$O$_3^-$M$^+$ or
(Uracyl)CH$_2$—S$_2$O$_3^-$M$^+$ or a hydrate thereof, where e=1–12 and "Uracyl" represents 2,4-dihydroxy-6-pyrimidyl or its keto-form equivalent.

8. A composite according to claim 1 in which the promoter comprises a compound having the formula $^+$M$^-$OOC(CH$_2$)$_h$—S$_2$O$_3^-$M$^+$ or
$^+$H$_3$N(CH$_2$)$_j$—S$_2$O$_3^-$M$^+$ or a hydrate thereof, where h=1–12 and j=2–12.

9. A composite according to claim 1 in which the metal is brass.

10. A composite according to claim 1 in which the diene rubber is natural or synthetic cis-polyisoprene or a blend of rubbers containing at least 25% by weight of cis-polyisoprene.

11. A composite according to claim 1 in which the amount of adhesion promoter is from 0.5 to 4 parts by weight per 100 parts by weight of rubber.

12. A composite according to claim 1 in which the amount of sulphur is from 2 to 6 parts by weight per 100 parts by weight of rubber.

13. A composite according to claim 1 containing a benzothiazole-2-sulphenamide as vulcanisation accelerator.

14. A composite according to claim 13 in which the benzothiazole-2-sulphenamide is N,N-dicyclohexylbenzothiazole-2-sulphenamide or 2(morpholinothio)benzothiazole, present in an amount of from 0.4 to 1.0 part by weight per 100 parts by weight of rubber.

15. An article in which vulcanised rubber is bonded to a metal, the article having been obtained by heating a composite according to claim 1 to vulcanise the rubber.

16. An article according to claim 15 that is a tire, the metal being brass coated on steel cords.

* * * * *